US007262292B2

(12) United States Patent
Pasupuleti et al.

(10) Patent No.: US 7,262,292 B2
(45) Date of Patent: Aug. 28, 2007

(54) OLIGONUCLEOTIDES AND METHODS FOR DETECTING HEPATITIS B VIRAL NUCLEIC ACIDS

(75) Inventors: Vijaya Pasupuleti, Irvine, CA (US); Hasnah Hamdan, Riverside, CA (US); Michael Lewinski, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 555 days.

(21) Appl. No.: 10/690,282

(22) Filed: Oct. 20, 2003

(65) Prior Publication Data

US 2005/0064437 A1 Mar. 24, 2005

Related U.S. Application Data

(63) Continuation of application No. 10/007,073, filed on Dec. 4, 2001, now Pat. No. 6,635,428.

(51) Int. Cl.
*C07H 212/04* (2006.01)
(52) U.S. Cl. ............... 536/24.33; 536/23.1; 536/23.72; 536/24.32
(58) Field of Classification Search ............... 536/23.1, 536/23.72, 24.32, 24.33
See application file for complete search history.

(56) References Cited

U.S. PATENT DOCUMENTS

| | | | | |
|---|---|---|---|---|
| 4,562,159 | A | 12/1985 | Shafritz | 436/501 |
| 4,683,195 | A | 7/1987 | Mullis et al. | 435/6 |
| 4,683,202 | A | 7/1987 | Mullis | 435/91 |
| 5,538,848 | A | 7/1996 | Livak et al. | 435/5 |
| 5,635,352 | A | 6/1997 | Urdea et al. | |
| 5,681,697 | A | 10/1997 | Urdea et al. | |
| 5,723,591 | A | 3/1998 | Livak et al. | 536/22.1 |
| 5,736,333 | A | 4/1998 | Livak et al. | 435/6 |
| 5,866,336 | A | 2/1999 | Nazarenko et al. | 435/6 |
| 5,876,930 | A | 3/1999 | Livak et al. | 435/6 |
| 5,952,202 | A | 9/1999 | Aoyagi et al. | 435/91.2 |
| 6,030,787 | A | 2/2000 | Livak et al. | 435/6 |
| 6,258,569 | B1 | 7/2001 | Livak et al. | 435/91.1 |

FOREIGN PATENT DOCUMENTS

| | | |
|---|---|---|
| JP | 103899-A/10 | 4/1999 |
| WO | WO89/04375 | 5/1989 |
| WO | WO90/13667 | 11/1990 |
| WO | WO91/10746 | 7/1991 |

OTHER PUBLICATIONS

Weinberber et al. J of Virulogic Methods 2000 vol. 85, pp. 75-82.*
SCORE Results from Sep. 28, 2006 of SEQ ID#6 result #5.*
Brunetto et al., "Does HbeAg Minus HBV Modify the Course of HDV Superinfection?"The Hepatitis Delat Virus, pp. 211-216, 1991.
Brunetto et al., "Wild-type and e Antigen-Minus Hepatitis B Viruses and Course of Chronic Hepatitis," Proc. Natl. Acad. Sci. USA, 88:4186-4190, 1991.
Chen et al., "Real Time PCR for Detection and Quantitation of Hepatitis B Virus DNA," Journal of Medical Virology, 65:250-256, 2001.
Chu et al., "Postsynthesis Functionalization of Oligonucleotides," Methods in Molecular Biology, 26:145-165, 1994.
Loeb et al., "High-Throughput Quantitative Analysis of Hepatitis B Virus DNA in Serum Using the TaqMan Fluorogenic Detection System," Hepatology, 32(3):626-629, 2000.
Meng et al., "Automated Multiplex Assay System for Simultaneous Detection of Hepatitis B Virus DNA, Hepatitis C Virus RNA, and Human Immunodeficiency Virus Type 1 RNA," Journal of Clinical Microbiology, 39(8)2 2937-2945, 2001.
Mercier et al., "Simultaneous Screening for HBV DNA and HCV RNA Genomes in Blood Donations Using a Novel TaqMan PCR Assay," Journal of Virological Methods, 77:1-9, 1999.
Pas et al., "Development of a Quantitative Real-Time Detection Assay for Hepatitis B Virus DNA and Comparison with Two Commercial Assays," Journal of Clinical Microbiology, 38(8):2897-2901, 2000.
Pasquinelli et al., "Hepatitis B Virus Infection of Peripheral Blood Mononuclear Cells is Common in Acute and Chronic Hepatitis," Journal of Medical Virology, 31:135-140, 1990.
Christian Oste, "Polymerase Chain Reaction," BioTechniques, 6:162-167, 1988.
Randall K. Saiki, "Amplification of Genomic DNA," PCR Protocols: A Guide to Methods and Applications, Academic Press, Chp. 2, pp. 13-20, 1990.
Saito et al., "Quantitative DNA Analysis of Low-Level Hepatitis B Viremia in Two Patients with Serologically Negative Chronic Hepatitis B," Journal of Medical Virology, 58:325-331, 1999.
Seelig et al., "Nachweis von Hepatitis-B-Virus-DNA mit der Polymerase-Kettenreaktion," DeutschMed Wochenschr, 115:1307-1312, 1990.
Sumazaki et al., "Detection of Hepatitis B Virus in Serum Using Amplification of Viral DNA by Means of the Polymerase Chain Reaction," Journal of Medical Virology, 27:304-308, 1989.
Theilmann et al., "Detection of HBV DNA in HBsAg-Positive Sera After Amplification Using the Polymerase Chain Reaction," Liver, 9:322-328, 1989.
van Schie et al., "Semiautomated Clone Verification by Real-Time PCR Using Molecular Beacons," BioTechniques, 29:1296-1308, 2000.

(Continued)

*Primary Examiner*—Bruce R. Campell
*Assistant Examiner*—Myron G. Hill
(74) *Attorney, Agent, or Firm*—Foley & Lardner LLP

(57) ABSTRACT

The present invention provides methods and compositions for determining the presence and/or amount of HBV nucleic acids in a test sample. In particular, substantially purified oligonucleotide primers and probes are described that can be used for qualitatively and quantitatively detecting HBV nucleic acid in a test sample by amplification methods. The present invention also provides primers and probes for generating and detecting control nucleic acid sequences that provide a convenient method for assessing internal quality control of the HBV assay.

12 Claims, No Drawings

OTHER PUBLICATIONS

Wharam et al., "Specific Detection of DNA and RNA Targets Using a Novel Isothemal Nucleic Acid Amplification Assay Based on the Formation of a Three-Way Junction Structure," Nucleic Acids Research, 29(11):1-8, 2001.

Zaaijer et al., "Comparison of Methods for Detection of Hepatitis B Virus DNA," Journal of Clinical Microbiology, 32(9):2088-2091, 1994.

Gong, Direct submission, NCBI, AF059603, 1-2, Jan. 30, 2000.

Drosten et al., "Evaluation of a New PCR Assay with Competitive Internal Control Sequence for Blood Donor Screening," Transfusion, 40:718-724, 2000.

Flordalisi et al., "High Genomic Variability in the Pre-C Region of Hepatits B Virus in Anit-HBe, HBV DNA Positive Chronic Hepatitis," Journal of Medical Virology, 31:297-300, 1990.

Hafner et al., "Isothermal Amplification and Multimerization of DNA by Bst DNA Polymerase," BioTechniques, 30:852-867, 2001.

Hileman et al., "Synthesis and Characterization of Conjugates Formed Between Periodate-Oxidized Ribonucleotides and Amine-Containing Fluorophores," Bioconjugate Chem., 5:436-444, 1994.

Honkoop et al., "Lamivudine Resistance in Immunocompetent Chronic Hepatitis B: Incidence and Patterns," Journal of Hepatology, 26:1393-1395, 1997.

Kaneko et al., "Detection of Serum Hepatitis B Virus DNA in Patients with Chronic Hepatitis Using the Polymerase Chain Reaction Assay," Proc. Natl. Acad. Sci. USA, 86:312-316, 1999.

Liang et al., "Characterization and Biological Properties of a Hepatitis B Virus Isolated From a Patient Without Hepatitis B Virus Serologic Markers," Hepatology, 12(2):204-212, 1990.

Keller et al., "Detection of Hepatitis B Virus DNA in Serum by Polymerase Chain Reaction Amplification and Microtiter Sandwich Hybridization," Journal of Clinical Microbiology, 28(6):1411-1416, 1990.

\* cited by examiner

OLIGONUCLEOTIDES AND METHODS FOR DETECTING HEPATITIS B VIRAL NUCLEIC ACIDS

This application is a continuation of U.S. Ser. No. 10/007,073, filed Dec. 4, 2001 now U.S. Pat. No. 6,635,428.

FIELD OF THE INVENTION

The present invention relates generally to compositions and methods for detecting hepatitis B viral nucleic acids in a test sample.

BACKGROUND OF THE INVENTION

The following discussion of the background of the invention is merely provided to aid the reader in understanding the invention and is not admitted to describe or constitute prior art to the present invention.

One of the major causes of hepatitis are specific hepatitis viruses. There are at least six different viruses responsible for various types of hepatitis. Among them, hepatitis B virus (HBV) is the most thoroughly characterized and complex etiologic agent. The infective Dane particle consists of a viral core plus an outer surface coat. The core contains circular double-stranded DNA and DNA polymerase, and it replicated within the nuclei of infected hepatocytes. Surface coat is added in the cytoplasm and is produced in great excess; it can be detected in serum by immunologic means as hepatitis. B surface antigen (HBsAg).

At least three distinct antigen-antibody systems are intimately related to HBV:

1. HBsAg is associated with the viral surface coat; its presence in serum is usually the first evidence of acute HBV infection and implies infectivity of the blood. HBsAg characteristically appears during the incubation period, usually 1 to 6 weeks before clinical or biochemical illness develops, and disappears during convalescence. The corresponding protective antibody (anti-HBs) appears weeks or months later, after clinical recovery, and usually persists for life; thus, its detection indicates past HBV infection and relative immunity;

2. Core antigen (HBcAg) is associated with the viral core. It can be found in infected liver cells but is not detectable in serum except by special techniques that disrupt the Dane particle. Antibody to HBcAg (anti-HBc) generally appears at the onset of clinical illness; thereafter, titers gradually diminish, usually for years or life. Its presence with anti-HBs is not significant beyond indicating previous HBV infection. It is also regularly found in chronic HBsAg carriers, who do not mount an anti-HBs response. In chronic infection, anti-HBc is mainly of the IgG class, whereas in acute infection, IgM anti-HBc predominates. Occasionally, IgM anti-HBc is the only marker of recent HBV infection, reflecting a "window" between disappearance of HBsAg and appearance of anti-HBs;

3. The e antigen (HBeAg) appears to be a peptide derived from the viral core. Found only in HBsAg-positive serum, HBeAg tends to parallel the production of viral DNA polymerase. Its presence, therefore, reflects more active viral replication and is generally associated with greater infectivity of the blood and a greater likelihood of progression to chronic liver disease. In contrast, presence of the corresponding antibody (anti-HBe) points to relatively lower infectivity and usually portends a benign outcome.

HBV is often transmitted parenterally, typically by contaminated blood or blood products. Routine screening of donor blood for HBsAg can dramatically diminish post-transfusion HBV infection. Hepatitis B virus (HBV) infects approximately 400 million persons worldwide. Chronic HBV carriers provide a world-wide reservoir of infection. Prevalence varies widely according to several factor, including geography. Vertical transmission from mother to infant is partly responsible, especially where prevalence is high.

HBV is associated with a wide spectrum of liver diseases, from a subclinical carrier state to acute hepatitis, chronic hepatitis, cirrhosis, and hepatocellular carcinoma (Loeb et al. Hepatology 32: 626-629, 2000). It also has a poorly understood association with several primarily nonhepatic disorders, including polyarteritis nodosa, and other collagen vascular diseases, etc. The pathogenic role of HBV in these disorders is not clear, but in some patients there is tissue deposition of immune complex containing viral antigen.

Hepatitis B is specifically diagnosed by identifying HBsAg in serum, with or without concomitant anti-HBc. Failure to detect HBsAg does not entirely exclude hepatitis B because antigenemia may be transient. Moreover, the presence of hepatitis B virus surface antigen (HBsAg) in serum or plasma indicates HBV infection, but the detection of HBsAg does not provide information on the replicative activity of the virus. Traditionally, the secretory version of the HBV core protein (HBeAg) serves as a marker for active viral replication. In the treatment of chronic hepatitis B, the presence or absence of HBeAg is assumed to represent a high or low replicative state of HBV, respectively. However, precore mutant HBVs which do not produce HBeAg, irrespective of their rate of replication, have been described (Zaaijer et al. J. Clin. Microbiol. 32: 2088-2091, 1994).

The measurement of HBV DNA in serum has become an important tool to identify individuals with high viral replication, to monitor patients on therapy, and to predict whether antiviral therapy will be successful. With the introduction of new antivirals like lamivudine [(−)2'3'-dideoxy-3'-thiacytidine], close monitoring of patients has become increasingly important due to the occurrence of antiviral drug-resistant virus strains or the presence of flares after withdrawal from antiviral therapy (Pas et al. J. Clin. Microbiol. 38: 2897-2901, 2000; Honkoop et al. J. Hepatology 26: 1393-1395, 1997).

Several tests have been employed to detect HBV in serum and other body fluids. Immunological tests are performed by demonstration of viral antigens (HBsAg, HBcAg and HBeAg), or their respective antibodies in serum.

Hybridization techniques have also been used. Generally, such techniques involve extracting DNA from cell scrapes or biopsy materials and immobilizing it on a solid phase either directly as total DNA or as restriction fragments after resolution by gel electrophoresis. The immobilized DNA is detected most commonly by a nucleic acid probe carrying a radioactive label. To increase the sensitivity of such assays, viral nucleic acid sequences can be amplified by using, for example, the polymerase chain reaction (PCR). The products thus obtained can be identified by using conventional hybridization techniques for identification of virus types, such as Southern blotting (C. Oste, BioTechniques 6: 163, 1988; K. B. Mullis, U.S. Pat. No. 4,683,202). PCR is described in U.S. Pat. Nos. 4,683,195 and 4,683,202 and has been utilized to improve the sensitivity of standard hybridization methods. U.S. Pat. No. 4,562,159 discloses a method and kit which use PCR to specifically detect HBV DNA in a test sample.

Several reports disclose assays of patient samples following a nucleic acid amplification step, such as PCR (Kaneko et al., Proc. Natl. Sci. U.S.A. 86: 312-316, 1989; Larzul et al., J. Virol. Meth. 20: 227-237; Sumazaki et al., J. Med. Virol. 27: 304-308, 1989; and Theilman et al., Liver 9: 322-328, 1989). Other relevant references describe amplification primers and detection probes for human HBV (Seelig et al., DeutschMed Wochenschr 115: 1307-1312, 1990; Brunetto et al., Proc. Natl. Acad. Sci., USA 88: 4186-4190, 1991; Brunetto et al., Prog. Clin. Biol. Res. (U.S.) 364: 211-216, 1991; Fiordalisi et al., J. Med. Virol. 31: 297-300, 1990; Liang et al., Hepatology 12(2): 204-212, 1990; Lo et al., J. Clin. Microbiol. 28(6): 1411-1416, 1990; Pasquinelli et al., J. Med. Virol 31: 135-140, 1990; Musso, PCT/US88/03735; Urdea, PCT/US90/02049; Urdea, et al., Gene 61: 253-264, 1987; and Urdea, PCT/US91/00213). The method and hybridization assays using self-quenching fluorescence probes with and/or without internal controls for detection of nucleic acid application products are known in the art, for example, U.S. Pat. Nos. 6,258,569; 6,030,787; 5,952,202; 5,876,930; 5,866,336; 5,736,333; 5,723,591; 5,691,146; and 5,538,848. Moreover, publications for detection of HBV using Real-time PCR (Taqman systems) include the following: Chen et al., J. Med. Virol. 65(2): 250-6, 2001; Meng et al., J. Clin Microbiol. 39(8): 2937-45, 2001; Loeb et al., Hepatology 32(3): 626-9, 2000; Pas et al., J. Clin Microbiol. 38(8): 2897-901, 2000; Drosten et al. Transfusion 40(6): 718-24, 2000; Weinberger et al., J. Virol Methods. 85 (1-2): 75-82, 2000; Saito et al., J. Med Virol. 58(4): 325-31, 1999; and Mercier et al. J. Virol Methods 77(1): 1-9, 1999.

SUMMARY OF THE INTVENTION

The present invention provides methods and compositions for determining the presence and/or amount of HBV nucleic acids in a test sample. In particular, substantially purified oligonucleotides for qualitatively and quantitatively detecting HBV nucleic acids in a test sample by amplification methods are described herein. The present invention can provide a specific, sensitive method that exhibits a broad dynamic range of detection of HBV nucleic acids, and which can advantageously provide quantitative as well as qualitative results.

In various embodiments of the present invention, oligonucleotide primers and probes are used in the methods described herein to provide the HBV assay. Thus, in certain embodiments, the invention relates to primer sequences that can be used to amplify HBV nucleic acids-present in a sample. These primer sequences are preferably hybrid primers that can also be used to amplify one or more control nucleic acid sequences, while simultaneously introducing HBV sequences into the control amplicon produced. By introducing HBV sequences into the control amplicon, the control can be be introduced into test samples and amplified by the same primers used to amplify the target HBV sequences, providing a convenient positive control.

In additional embodiments, the invention relates in part to probe nucleic acids that can be conjugated to a detectable label preferably, a fluorescent dye, and most preferably a dye pair located at the 5' and 3' end of the oligonucleotides. Certain labeled oligonucleotides are described that hybridize to amplified HBV nucleic acids, if present, in the sample. Similarly, certain labeled oligonucleotides are described that hybridize to a control amplicon that may have been introduced into the test sample as a positive control.

In a first aspect, the invention relates to a composition of one or more substantially purified oligonucleotides having sequences selected from the following group:

5'-TCC TCC AAT TTG TCC TGG TTA TCG CT-3' (SEQ ID NO:3), a HBV sequence (Weinberger et al., J. Virol Methods 85(1-2): 75-82, 2000);

5'-CAA CCT CCA ATC ACT CAC CAA CTG CCG GAG CGG ACA TTA CAA ACG-3' (SEQ ID NO:4), a hybrid nucleic acid comprising both HBV and phage lambda sequences;

5'-ATA TGA TAA AAC GCC GCA GAC ACA AAA TCC GGT AGT AAC TTG CTA ACC-3' (SEQ ID NO:5)), a hybrid nucleic acid comprising both HBV and phage lambda sequences; and 5'-TAG GCA GGT CAT TGG CAA CAG TG-3' (SEQ ID NO:6), a phage lambda sequence.

In preferred embodiments, one or more of the selected oligonucleotides can be conjugated to a detectable label, preferably a fluorescent dye, and most preferably a dye pair. Particularly preferred oligonucleotide dye conjugates are 5'[6-carboxyfluoresceine (FAM)]-TCC TCC AAT TTG TCC TGG TTA TCG CT-[6-carboxytetramethylrhodanine (TAMRA)]3' (SEQ ID NO:7, Weinberger et al., J. Virol Methods 85(1-2): 75-82, 2000); and 5'[6-carboxy, 4'5'dichloro 2',7' dimethoxy rhodamine (JOE)]-TAG GCA GGT CAT TGG CAA CAG TG-[6-carboxytetramethylrhodamine (TAMRA)]3' (SEQ ID NO:8). These may be used as probes for HBV and phage lambda, respectively, in methods to detect the presence or amount of specific nucleic acids present in a test sample.

In another aspect, the present invention relates in part to methods that use hybrid HBV-phage lambda nucleic acid primers to produce hybrid amplicons comprising a core phage lambda sequence, flanked by HBV sequences. In preferred embodiments, oligonucleotides having the sequences 5'-CAA CCT CCA ATC ACT CAC CAA CTG CCG GAG CGG ACA TTA CAA ACG-3' (SEQ ID NO:4) and 5'-ATA TGA TAA AAC GCC GCA GAC ACA AAA TCC GGT AGT AAC TTG CTA ACC-3' (SEQ ID NO:5) are used as primers to amplify a sample of phage lambda nucleic acid to produce the hybrid amplicons.

In certain embodiments, HBV-phage lambda hybrid amplicons can be prepared and purified for use in HBV assays. In these embodiments, hybrid amplicon nucleic acid can be introduced into a sample to be analyzed for the presence or amount of HBV DNA. Because of the flanking HBV sequences present in the hybrid amplicon, primers can be selected that can amplify both the hybrid nucleic acid added, as well as any HBV present in the sample. Depending on the timing at which the hybrid nucleic acid is introduced into the sample, the hybrid nucleic acid can serve as a positive control for nucleic acid extraction from the sample, and/or for an HBV amplification reaction.

In another aspect, the present invention relates in part to methods for detecting the presence or amount of HBV nucleic acid present in a test sample. These methods preferably comprise amplifying HBV nucleic acids if present in said sample using a pair of oligonucleotide primers; hybridizing said amplified HBV nucleic acids with an oligonucleotide probe; and detecting a signal from said hybridized HBV nucleic acids, wherein the signal is related to the presence or amount of HBV nucleic acids in the test sample.

In various preferred embodiments, the oligonucleotide primers have the sequences 5'-CAA CCT CCA ATA ACT CAC CAA C-3' (SEQ ID NO:1) and 5'-ATA TGA TAA AAC GCC GCA GAC AC-3' (SEQ ID NO:2); the oligonucleotide probe has the sequence 5'-TCC TCC AAT TTG TCC TGG TTA TCG CT-3' (SEQ ID NO:3); the oligonucleotide probe comprises a detectable label; the oligonucleotide probe has the sequence 5'(FAM)-TCC TCC AAT TTG TCC TGG TTA TCG CT-(TAMRA)3' (SEQ ID NO:7); a positive control nucleic acid is introduced into the test sample prior to amplification of HBV sequences; the positive control nucleic acid is a HBV-phage lambda hybrid; the positive control nucleic acid is amplified by the same primers used to amplify the HBV sequences; the positive control nucleic acid is detectable using an oligonucleotide probe having the sequence 5'-TAG GCA GGT CAT TGG CAA CAG TG-3' (SEQ ID NO:6); and/or the positive control nucleic acid is detected using an oligonucleotide probe having the sequence 5'(JOE)-TAG GCA GGT CAT TGG CAA CAG TG-(TAMRA)$_3$' (SEQ ID NO:8).

In yet another aspect of the present invention, a "real time PCR" assay providing dynamic fluorescence detection of amplified HBV products produced in a PCR amplification reaction is described. During PCR, the amplified products hybridize to probe nucleic acids, which are labeled with both a reporter dye and a quencher dye. When these two dyes are in close proximity, i.e. both are present in an intact probe oligonucleotide, the fluorescence of the reporter dye is suppressed. However, a polymerase, such as AmpliTaq Gold™, having 5'-3' nuclease activity can be provided in the PCR reaction. This enzyme cleaves the fluorogenic probe if it is bound specifically to the target nucleic acid sequences between the priming sites. The reporter dye and quencher dye are separated upon cleavage, permitting fluorescent detection of the reporter dye. Upon excitation by a laser provided, e.g., by a sequencing apparatus, the fluorescent signal produced by the reporter dye is detected and/or quantified. The increase in fluorescence is a direct consequence of amplification of target nucleic acids during PCR.

In various preferred embodiments, the oligonucleotide primers used in the PCR amplification have the sequences 5'-CAA CCT CCA ATA ACT CAC CAA C-3' (SEQ ID NO:1) and 5'-ATA TGA TAA AAC GCC GCA GAC AC-3' (SEQ ID NO:2); the reporter dye is FAM and the quencher dye is TAMRA; the HBV oligonucleotide probe has the sequence 5'(FAM)-TCC TCC AAT TTG TCC TGG TTA TCG CT-(TAMRA)3' (SEQ ID NO:7); a positive control nucleic acid is introduced into the test sample prior to PCR amplification of HBV sequences; the positive control nucleic acid is a HBV-phage lambda hybrid; the positive control nucleic acid is amplified by the same primers used to amplify the HBV sequences; the reporter dye is JOE and the quencher dye is TAMRA; and/or the positive control nucleic acid is detected using an oligonucleotide probe having the sequence 5'(JOE)-TAG GCA GGT CAT TGG CAA CAG TG-(TAMRA)3' (SEQ ID NO:8).

In yet another aspect, the methods and compositions for detecting and/or quantifying HBV virus of the present invention can be used for designing a treatment regimen. In particular, the detection of the presence or amount of HBV nucleic acid in a biological sample following a selected treatment(s) can be used to assess the success or lack thereof in the treatment regimen. The present invention can also be used to compare the relative presence or amount of HBV nucleic acids in a patient before and after such a treatment regimen. Similarly, methods and compositions described herein can be used for screening therapeutic compounds. In particular, the quantitative detection of the presence or amount of HBV nucleic acids in a biological sample following administration of one or more compounds can be used to assess therapeutic efficacy. The present invention can also be used to compare the relative presence or amount of HBV nucleic acids in a patient before and after administration of one or more compounds.

In another aspect, the present invention relates in part to kits comprising sufficient materials for performing one or more methods described herein. In preferred embodiments, a kit includes one or more materials selected from the following group in an amount sufficient to perform at least one HBV assay: Oligonucleotide primers having the sequences 5'-CAA CCT CCA ATA ACT CAC CAA C-3' (SEQ ID NO:1) and 5'-ATA TGA TAA AAC GCC GCA GAC AC-3' (SEQ ID NO:2); an oligonucleotide probe having the sequence 5'-TCC TCC AAT TTG TCC TGG TTA TCG CT-3' (SEQ ID NO:3); an oligonucleotide probe having the sequence 5'(FAM)-TCC TCC AAT TTG TCC TGG TTA TCG CT-(TAMRA)3' (SEQ ID NO:7); a positive control nucleic acid to be introduced into a test sample prior to amplification of HBV sequences; a positive control nucleic acid that is a HBV-phage lambda hybrid; a positive control nucleic acid that is detectable using an oligonucleotide probe having the sequence 5'-TAG GCA GGT CAT TGG CAA CAG TG-3' (SEQ ID NO:6); a positive control nucleic acid that is detected using an oligonucleotide probe having the sequence 5'(JOE)-TAG GCA GGT CAT TGG CAA CAG TG-(TAMRA)3' (SEQ ID NO:8);

DETAILED DESCRIPTION OF THE PREFERRED EMBODIMENTS

The present invention provides methods and compositions for the rapid and sensitive determination of HBV nucleic acids in test samples. In particular, oligonucleotide probes and primers are described that can be used in a method for quantitatively or qualitatively detecting HBV nucleic acids in a sample. The present invention also provides primers and probes for generating and detecting control nucleic acid sequences that provide a convenient method for assessing internal quality control of the HBV assay.

As used herein, the term "HBV-phage lambda nucleic acid hybrids" refers to chimeric nucleic acid molecules containing both HBV and lambda phage nucleic acids sequences. Preferred HBV-phage lambda hybrids comprise a core sequence from phage lambda, flanked by HBV sequences having sufficient length to hybridize to amplification primers.

As used herein, the term "substantially purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

As used herein, the term "oligonucleotides" refers to a short polymer composed of deoxyribonucleotides, ribonucleotides or any combination thereof. These oligonucleotides are at least 9 nucleotides in length, preferably 20 to 70 nucleotides long, with 21 to 26 nucleotides being the most common. In certain embodiments, the oligonucleotides are joined together with a detectable label.

As used herein, the term "HBV nucleic acids" refers to DNA and/or RNA comprising a contiguous sequence from a hepatitis B virus genome, or the complement thereof. HBV nucleic acids may be HBV genomic DNA, HBV messenger RNA, or the complement of these sources, obtained by any method including obtaining the nucleic acid from a biological source, synthesizing the nucleic acid in vitro, or amplifying the nucleic acid by any method known in the art.

As used herein, the term "hybridize" refers to process that two complementary nucleic acid strands anneal to each other under appropriately stringent conditions. Hybridizations are typically and preferably conducted with probe-length nucleic acid molecules, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "stringent hybridization conditions" as used herein refers to hybridization conditions at least as stringent as the following: hybridization in 50% formaamide, 5×SSC, 50 mM NaH2PO4, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "amplify" with respect to nucleic acid sequences refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1;29(11):E54-E54; Hafner et al., Biotechniques 2001 Apr.;30(4):852-6, 858, 860 passim; Zhong et al., Biotechniques 2001 Apr.; 30(4):852-6, 858, 860 passim.

As used herein, the term "test sample" refers to any liquid or solid material believed to comprise HBV nucleic acids. In preferred embodiments, a test sample is obtained from a biological source, such as cells in culture or a tissue sample from an animal, most preferably, a human. Preferred sample tissues of the instant invention include, but are not limited to, plasma, serum, whole blood, blood cells, lymphatic fluid, cerebrospinal fluid, synovial fluid, urine, saliva, and skin or other organs (e.g. biopsy material). The term "patient sample" as used herein refers to a tissue sample obtained from a human seeking diagnosis or treatment of a disease related to a HBV infection.

The term "detectable label" as used herein refers to a composition or moiety that is detectable by spectroscopic, photochemical, biochemical, immunochemical, electromagnetic, radiochemical, or chemical means such as fluorescence, chemifluoresence, or chemiluminescence, or any other appropriate means. Preferred detectable labels are fluorescent dye molecules, or fluorochromes, such fluorescein, phycoerythrin, CY3, CY5, allophycocyanine, Texas Red, peridenin chlorophyll, cyanine, FAM, JOE, TAMRA, tandem conjugates such as phycoerythrin-CY5, and the like. These examples are not meant to be limiting.

The term "fluorochrome" as used herein refers to a molecule that absorbs a quantum of electromagnetic radiation at one wavelength, and emits one or more photons at a different, typically longer, wavelength in response. In preferred embodiments, a fluorochrome can be a member of a pair of physically linked fluorochromes that exhibit fluorescence energy transfer. An energy transfer pair may be excited by a quantum of electromagnetic radiation at a wavelength at which the donor fluorochrome is excited; however, fluorescence from the donor fluorochrome that would be expected in the absence of the acceptor is quenched at least in part, and emission at an emission wavelength of the acceptor fluorochrome is observed.

In particularly preferred embodiments, a fluorochrome is one member of a physically linked "molecular beacon" pair. In these embodiments, the molecular beacon pair may be excited by a quantum of electromagnetic radiation at a wavelength at which a first fluorochrome member of the pair is excited; however, fluorescence from the first fluorochrome that would be expected in the absence of the second fluorochrome is quenched at least in part. Unlike energy transfer pairs, however, emission at an emission wavelength of the acceptor fluorochrome is not observed. Thus, these labels comprise a pair of dyes, one of which is referred to as a "reporter," and the second of which is referred to as a "quencher." When the two dyes are held in close proximity, such as at the ends of a nucleic acid probe, the quencher moiety prevents detection of a fluorescent signal from the reporter moiety. When the two dyes are separated, however, the fluorescent signal from the reporter moiety becomes detectable.

The term "linker" as used herein refers to one or more chemical bonds or a chemical group used to link one moiety to another, serving as a divalent bridge, where it provides a group between two other chemical moieties.

Sample Preparation:

The presence or amount of HBV nucleic acids in a sample can be determined by amplifying the target regions within the HBV gene. Thus, any liquid or solid material believed to comprise HBV nucleic acids can be an appropriate sample. Preferred sample tissues include plasma, serum, whole blood, blood cells, lymphatic fluid, cerebral spinal fluid, synovial fluid and others.

Such sample will often be taken from patients suspected of having HBV infection, or having a wide spectrum of liver diseases related to HBV infection. Such diseases include a subclinical carrier state, acute hepatitis, chronic hepatitis, cirrhosis, and hepatocellular carcinoma. Although the pathogenetic role of HBV is not clear, HBV is also associated with several primarily nonhepatic disorders which include polyarteritis nodosa and other collagen vascular diseases, membranous glomerulonephritis, essential mixed cryoglobulinemia, and papular acrodermatitis of childhood.

Nucleic acids representing the HBV gene of interest may be extracted from tissue samples. Various commercial nucleic acid purification kits, such as QIAmp 96 Virus BioRobot Kit and Qiagen's BioRobot 9604 are known to the skilled artisan, and used to isolate HBV nucleic acids from samples.

Amplification of HBV Nucleic Acids of Interest:

Target samples or isolated nucleic acids may be amplified by various methods known to the skilled artisan. Preferably, PCR is used to amplify HBV nucleic acids of interest. In this method, two or more oligonucleotide primers that flank and bind to opposite strands of a nucleic acid of interest are repetitively annealed to their complementary sequences, extended by a DNA polymerase, and heat denatured, resulting in exponential amplification of the target nucleic acid sequences. The skilled artisan is capable of designing and preparing primers that are appropriate for amplifying a target sequence. In preferred embodiment of the instant invention, primers are designed for amplifying regions within the HBV surface gene that show maximum sequence conservation. These primers in the HBV genome are identical with more than 95% of all published HBV gene sequences (as contained in GenBank release 110.0, 12/98). Cycling parameters can be varied, depending on the length of nucleic acids to be extended.

Hybridization Probes With a Detectable Label

Oligonucleotide probes complementary and hybridizing to the amplified target HBV nucleic acids are conjugated to a detectable label. Preferably, the detectable label is a fluorescence dye. Particularly preferred are detectable labels known as "molecular beacons." These labels comprise a pair of dyes, one of which is referred to as a "reporter," and the second of which is referred to as a "quencher." When the two dyes are held in close proximity, such as at the ends of a nucleic acid probe, the quencher moiety prevents detection of a fluorescent signal from the reporter moiety. When the two dyes are separated, however, the fluorescent signal from the reporter moiety becomes detectable.

Molecular beacons can be utilized during PCR, for example, by using a DNA polymerase that cleaves a probe nucleic acid if it is bound specifically to the target nucleic acid sequence. Quantitative real-time PCR is based on detection of a fluorescent signal produced proportionally during the amplification of a PCR product. A probe is designed to anneal to the target sequence between the traditional forward and reverse primers. The probe is labeled at the 5' end with a reporter fluorochrome, and a quencher fluorochrome is added at any other position (or at the 3' end). The probe is designed to have a higher Tm than the primers. As long as both fluorochromes are on the probe, the quencher molecule stops all fluorescence by the reporter. However, as Taq polymerase extends the primer, the intrinsic 5' to 3' nuclease activity of Taq degrades the probe, releasing the reporter fluorochrome. The amount of fluorescence released during the amplification cycle is proportional to the amount of product generated in each cycle. See, e.g., van Schie et al., Biotechniques 29: 1296-1300 (2000).

Methods for attaching detectable labels are well known in the art. For example, fluorochromes may be attached. See, e.g., Chu et al., Methods Mol. Biol. 26, 145-165 (1994); Hileman et al., Bioconjug. Chem. 5, 436-444 (1994).

Preparation Of An Internal Control

As a quality control measure, an internal amplification control may be included in one or more samples to be extracted and amplified. While hybrid HBV-phage lambda nucleic acid are described herein, the skilled artisan will understand that any detectable sequence that is not derived from HBV can be used as the control sequence. A control sequence can be produced synthetically, but is preferably produced by amplifying the control sequence, e.g., lambda phage DNA, using a pair of primer sequences comprising lambda phage sequence flanked by HBV primer target sequences. The resulting hybrid nucleic acids comprise a lambda phage sequence flanked by sequences that hybridize to an HBV primer sequence. These controls can be mixed with sample (or purified nucleic acids isolated from the sample), and amplified with sample nucleic acids using a pair of HBV primers. If PCR amplification is successful, the internal amplification control amplicons can then be detected and differentiated from HBV sequences using a probe to the phage sequence. Additionally, if included in the sample prior to purification of nucleic acids, the control sequences can also act as a positive purification control.

HBV Assay

In preferred embodiments, the HBV specific primers are shown in SEQ ID:1 and SEQ ID:2, although the skilled artisan will understand that other probes may be used. Stock HBV standard curve dilutions may be run simultaneously. The methods described herein can provide qualitative and quantitative results over the range of about 200 to about 500,000,000 HBV target nucleic acid copies/mL.

EXAMPLES

Example 1

Sample Collection and Preparation

Blood was collected in a sterile tube without anticoagulant and allowed to clot. The serum was separated from the clot within 1 hour of collection and immediately stored at −20° or colder in a sterile screw-capped cryogenic vial. Repeated freeze-thawing should be avoided.

Generally, serum was stored up to three days at 2-8°. For longer term storage, serum was frozen at −20° C. or colder. Frozen specimens were thawed at 20-25° C. or in water at room temperature. Self defrosting freezers were not recommended. To prevent cross contamination, no aliquot was ever returned to the original container.

QIAmp 96 Virus BiORobot Kit and Qiagen's BiORobot 9604 was used to isolate DNA from serum samples. Each sample was lysed in the presence of QIAGEN protease and Buffer AL (a low pH buffered solution containing chaotropic salt and detergent, Qiagen) under highly denaturing conditions. The lysate buffering conditions were adjusted to allow binding of the DNA to the QIAmp membrane by addition of ethanol. DNA was absorbed on the silica-gel membrane using vacuum. Salt and pH conditions in the lysate ensured that impurities which could inhibit PCR were not retained on the membrane, DNA bound to the membrane was washed using vacuum and centrifugation. Highly purified DNA was eluted in 200 μl of Elution buffer (Nuclease free water). All the working reagents were prepared using the methods described in the Kit.

Alternatively, HBV DNA can be isolated in accordance with manual Qiagen extraction using QIAamp DNA Blood mini kit. Basically, 20 μl QIAGEN protease was pipetted into the bottom of a 1.5 ml microcentrifuge tube. A 200 μl serum sample was then added into the tube with another 200 μl buffer AL, mixed by vortexing, and then incubated at 56° C. for 10 minutes. 200 μl Ethanol (96-100%) was added into the mixture.

The mixture was then carefully applied to the QIAamp spin column (in a 2.0 ml collection tube) and centrifuged at 6000×g (8000 rpm) for 1 minute. The QIAamp spin column was placed in a clean 2.0 ml collection tube after the centrifugation. 500 μl Buffer AW1 (a low pH buffered solution containing chaotropic salt and detergent, Qiagen), was added, and the mixture was centrifuged at 6000×g (8000 rpm) for 1 minute. The spin column was placed in another clean 2.0 ml collection tube, 500 μl Buffer AW2 (a buffered solution of chaotropic salt and ethanol, Qiagen) was added and the mixture centrifuged at 13,000 rpm for 3 minutes. The spin column was placed in another 2.0 ml collection tube and centrifuged again at 13,000 rpm for 1 minute.

The spin column was then placed in a clean 1.5 ml microcentrifuge tube. The HBV DNA was eluted with 200 μl nuclease free water by applyed the water into the column, incubated it at room temperature for 1 minute, and then centrifuged at 6000×g (8000 rpm) for 1 minute. The HBV DNA can be used for amplification immediately or can be stored at −20° C.

Example 2

Preparation for HBV Real-Time PCR and Fluorogenic Probe Hybridization

A master mixture of reagents for performing PCR, and further hybridization with the fluorogenic probe was prepared and shown in Table 1. The mixture was dispensed in 1.0 ml aliquots and stored at −20° C. It is stable for one year. The fluorogenic probes were synthesized by Applied Biosystems. The fluorescein dyes used in the instant invention include but not limited to 6-carboxyfluorescein (6-FAM), 5'-dichloro-6-carboxyrhodamine (JOE), 2'-chloro-7'-phenyl-1,4-dichloro-6-carboxyfluorescein (VIC). Another preferred class of labels include quencher moieties. The emission spectra of a quencher moiety overlaps with a proximal intramolecular or intermolecular fluorescent dye such that the fluorescence of the fluorescent dye is substantially diminished, or quenched, by fluorescence resonance energy transfer (FRET). Oligonucleotides which are intramolecularly labeled with both fluorescent dye and quencher moieties are useful in nucleic acid hybridization assays, e.g. the "Taqman" exnuclease-cleavage PCR assay (U.S. Pat. Nos. 5,723,591; 5,538,848). The quencher moieties used in the instant invention include but not limited to tetramethyl-6-carboxyrhodamine (TAMRA).

TABLE 1

HBV/fluorogenic probe master mixture.

| Reagent | ×1 (µl) | ×100 (µl) |
|---|---|---|
| Nuclease free water (Biowhittaker) | 7.58 | 758 |
| 10 × PCR Buffer II | 5.00 | 500 |
| 25 mM MgCl2 | 6.00 | 600 |
| 2/4 mM dUTPs | 5.00 | 500 |
| HBV-F primer (25 µM) | 0.20 | 20 |
| HBV-R primer (25 µM) | 0.20 | 20 |
| HBV probe (25 µM) | 0.06 | 6 |
| Lambda probe (25 µM) | 0.06 | 6 |
| 6-Rox (50 µM) | 0.15 | 15 |

In the mixture, the HBV-F primer has the nucleic acid sequence of 5'-CAA CCT CCA ATC ACT CAC CAA-3' (SEQ ID NO:1), and HBV-R primer has the nucleic acid sequence of 5'-ATA TGA TAA AAC GCC GCA GAC AC-3' (SEQ ID NO:2). The HBV-probe is 5'[FAM]-TCC TCC AAT TTG TCC TGG TTA TCG CT-[TAMRA]3' (SEQ ID NO:7). The lambda probe is 5'[JOE]-TAG GCA GGT CAT TGG CAA CAG TG-[TAMRA]3' (SEQ ID NO:8).

To perform the real time PCR, sufficient aliquots (1.0 ml) of the HBV/fluorogenic probe master mixture was thawed at room temperature. 22 µl Amperase (UNG) and 11 µl Amplitaq Gold™ DNA polymerase were added into the master mixture (usually sufficient for 40 reactions). Since the fluorogenic probes in the master mix degrade when left for more than an hour at room temperature, the mix was stored (4-8° C.) until used.

Real time PCR was performed in a Taqman 7700 instrument. The reaction mixture contained 25 µl of HBV/fluorogenic master mixture with UNG and Amplitaq Gold™ DNA polymerase, and 25 µl of DNA template or nuclease free water (control). The total volume of the reaction was 50 µl. The thermal cycler conditions were as follows: stage 1: 50° C. for 2 minutes; stage 2: 95° C. for 10 minutes; stage 3: 45 cycles of 95° C. for 15 seconds and 60° C. for 1 minute. The operation of the Taqman 7700 was as described in the manual. The run hours were about 2 hours and 10 minutes.

Example 3

Preparation of an Internal Control

Lambda phage-HBV nucleic acid hybrids were produced in this example as an internal control. In order to make the lambda-phage HBV nucleic acid hybrids, the lambda DNA was denatured for 10 min at 65° C. followed by quick cooling on ice for 5 min, and amplified using a pair of primers comprising lambda phage sequences with HBV primer sequences on both ends. The master mixture for the preparation of lambda phage-HBV nucleic acid hybrids is shown in Table 2.

| Reagent | ×1 (µl) | ×10 (µl) |
|---|---|---|
| Nuclease free water | 31.55 | 315.5 |
| 10 × PCR buffer II | 5.00 | 50.0 |
| 25 mM MgCl2 | 6.00 | 60.0 |
| 25 mM dNTPs | 2.00 | 20.0 |
| Lambda-HBV-F primer (25 µM) | 1.60 | 16.0 |
| Lambda-HBV-R primer (25 µM) | 1.60 | 16.0 |
| Taq DNA polymerase (5 U/µl) | 0.25 | 2.5 |
| Total | 48.0 | 480.0 |

The lambda-HBV-F primer used herein had the nucleic acid sequence of 5'-CAA CCT CCA ATC ACT CAC CAA CTG CCG GAG CGG ACA TTA CAA ACG-3' (SEQ ID NO:4), and the lambda-HBV-R primer used herein had the nucleic acid sequence of 5'-ATA TGA TAA AAC GCC GCA GAC ACA AAA TCC GGT AGT AAC TTG CTA ACC-3' (SEQ ID NO:5).

2 µl denatured lambda DNA (10 ng/µl) was added to 48 µl of master mixture and amplified using the following thermocycling conditions on a PE 9600 thermocycler: incubation at 95° C. for 1 minute followed by 35 cycles each composed of 95° C. for 30 seconds, 57° C. for 30 seconds and 72° C. for 1 minute, then elongation at 72° C. for 10 minutes followed by a cool down at 4° C.

The success of the PCR reaction was verified by running 10 µl of the PCR products on 2% NuSieve 3:1 agarose gel. PCR amplification for lambda phage DNA showed a single band of 140 bp. This lambda-HBV nucleic acids hybrids were purified and concentrated using Microcon microconcentrator (Amicon), which employ Amicon's low-binding, anisotropic, hydrophilic YN-100 membrane.

Example 5

Preparation of HBV Standard

In addition to the internal control, other control samples were also included. For example, HBV negative control serum, a normal human serum tested and found to be negative for HbsAg, anti-HIV1/2 and anti-HCV by U.S. FDA licensed test procedure; BBI low (+) control serum, Accurun® 325 HBV DNA Positive Marker (Series 300) containing 1,000 copies/ml of HBV DNA virus; and BBI high (+) control serum, Accurun® 325 HBV DNA Positive Marker (Series 700) containing 10,000,000 copies/ml of HBV DNA virus were analyzed by the described methods. Control serum were supplied by Boston Biomedica, Inc. An HBV control (5×10⁸ copies/ml) was also provided and diluted 1:10 with negative serum.

An-HBV standard was prepared as follows: patient serum was pooled with HBV values>2000 pg/ml (>5.6×10⁸ copies/mL) as determined by Digene HBV quantitation assay (Nichols Institute TC3200). The pooled serum was diluted 1:1 with BBI negative serum. Further dilutions were made if necessary. At least five replicates were run in three separate assays to assign a value. The target value should be about 1800 pg/ml or 5×10⁸ copies/ml for working standard. The following conversion factors were used to convert pg/ml to copies/ml: 5 pg/ml=1.4×10⁶ copies/ml and 1 pg/ml 2.8×10⁵ copies/ml. For example, 1800 pg/ml=1800×(2.8× $10^5$)=5×10⁸ copies/ml.

The series dilutions for standard curve are shown in Table 3.

| Standard name (replicates run) | Final value (copies/ml) | Amount of stock | Amount of negative serum | Total volume for 100 runs | Aliquot volume | # of aliquots |
|---|---|---|---|---|---|---|
| A | 5 × 10⁸ | Initial stock | | | | |
| B | 5 × 10⁷ | 1.0 ml of A | 9.0 ml | | | |
| C (2) | 5 × 10⁶ | 7.0 ml of B | 63 ml | 60 ml | 0.7 ml | 85 |
| D | 5 × 10⁵ | 2.0 ml of C | 18 ml | | | |
| E (3) | 5 × 10⁴ | 15 ml of D | 135 ml | 90 ml | 1.0 ml | 90 |
| F | 5 × 10³ | 5 ml of E | 45 ml | | | |
| G (3) | 5 × 10² | 20 ml of F | 180 ml | 90 ml | 1.0 ml | 90 |
| H (4) | 200 | 52 ml of G | 78 ml | 120 ml | 1.5 ml | 80 |

Example 6

Data Analysis and Reporting

After the PCR reaction finished, the JOE dye layer was checked to confirm successful amplification of internal control sequences. The correlation coefficient for the standard curve was 0.95 or greater in each valid amplification. The average threshold cycle (Ct.) for each standard is as follows:

| Standard | Copies/ml | Average Ct. value |
|---|---|---|
| A | 5000,000,000 | 15.8 ± 1 |
| C | 5,000,000 | 22.4 ± 1 |
| E | 50,000 | 29.4 ± 1 |
| G | 500 | 35.1 ± 1 |
| H | 200 | 37.2 ± 1 |

In summary, the measurement of HBV DNA in serum is used to quantitate HBV viral replication, monitor therapy and predict the success of antiviral therapy. The method used to quantitate HBV DNA in this test is PCR. The test has a linear range of 200 to 500,000,000 copies/ml, and can be correlated to the HBV DNA Hybrid capture assay (Digene) by relating 1 pg/ml=280,000 copies/ml.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. An oligonucleotide of between 20 to 70 nucleotides in length and having a sequence selected from the group consisting of:

```
                                                       (SEQ ID NO:4)
5'-CAA CCT CCA ATC ACT CAC CAA CTG CCG GAG CGG ACA

TTA CAA ACG-3', and (SEQ ID NO:5)
5'-ATA TGA TAA AAC GCC GCA GAC ACA AAA TCC GGT AGT

AAC TTG CTA ACC-3'
```

2. The oligonucleotide of claim 1, wherein said oligonucleotide is conjugated to a detectable label.

3. The oligonucleotide of claim 2, wherein the detectable label is a fluorescent dye.

4. The oligonucleotide of claim 2, wherein the detectable label is a fluorescent energy transfer dye pair.

5. The oligonucleotide of claim 1, wherein said oligonucleotide is SEQ ID NO:4.

6. The oligonucleotide of claim 1, wherein said oligonucleotide is SEQ ID NO:5.

7. An oligonucleotide having a nucleotide sequence consisting essentially of 5'-TAG GCA GGT CAT TGG CAA CAG TG-3' (SEQ ID NO:6).

8. The oligonucleotide of claim 7, wherein the detectable label is a fluorescent energy transfer dye pair.

9. The oligonucleotide of claim 7, wherein said oligonucleotide is conjugated to a detectable label.

10. The oligonucleotide of claim 7, wherein the detectable label is a fluorescent dye.

11. The oligonucleotide of claim 7, wherein said oligonucleotide is SEQ ID NO:6.

12. The oligonucleotide of claim 8, wherein the oligonucleotide is 5' [6-carboxy, 4'5'dichloro 2',7' dimethoxy fluresceine (JOE)]-TAG GCA GGT CAT TGG CAA CAG TG-[6-carboxytetramethylrhodamine (TAMRA)]3'.

* * * * *

SEQUENCE LISTING

<160> NUMBER OF SEQ ID NOS: 8

<210> SEQ ID NO 1
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caacctccaa taactcacca ac                                              22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atatgataaa acgccgcaga cac                                             23

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tcctccaatt tgtcctggtt atcgct                                          26

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caacctccaa tcactcacca actgccggag cggacattac aaacg                     45

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atatgataaa acgccgcaga cacaaaatcc ggtagtaact tgctaacc                  48

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
taggcaggtc attggcaaca gtg                                             23

<210> SEQ ID NO 7
<211> LENGTH: 26
<212> TYPE: DNA
```

-continued

```
<213> ORGANISM: Artificial Sequence
<220> FEATURE:
<223> OTHER INFORMATION: Description of Artificial Sequence: Synthetic
      probe

<400> SEQUENCE: 7
tcctccaatt tgtcctggtt atcgct                                            26

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
taggcaggtc attggcaaca gtg                                               23
```